United States Patent [19]
Ueno et al.

[11] Patent Number: 5,304,388
[45] Date of Patent: Apr. 19, 1994

[54] METHOD FOR MANUFACTURING POWDERY CRYSTALLINE MALTITOL

[75] Inventors: Ryuzo Ueno, Nishinomiya; Tomoe Kanno, Ushiku; Yuji Kunimi, Ushiku; Akihiko Tabata, Ushiku, all of Japan

[73] Assignee: Kabushiki Kaisha Ueno Seiyaku Oyo Kenkyuio, Osaka, Japan

[21] Appl. No.: 32,785

[22] Filed: Mar. 17, 1993

[30] Foreign Application Priority Data

Mar. 17, 1992 [JP] Japan .................................. 4-60129

[51] Int. Cl.$^5$ .................... A23L 1/09; A61K 31/70
[52] U.S. Cl. ................................. 426/658; 536/124; 127/40; 426/660; 426/804
[58] Field of Search ............. 426/658, 804, 660; 536/124; 127/40

[56] References Cited

U.S. PATENT DOCUMENTS

| | | | |
|---|---|---|---|
| 4,717,765 | 1/1988 | Hirao et al. | 536/124 |
| 4,831,129 | 5/1989 | Serpelloni | 536/124 |
| 4,846,139 | 7/1989 | Devos et al. | 127/40 |
| 5,084,563 | 1/1992 | Sakai et al. | 536/4.1 |
| 5,137,723 | 8/1992 | Yamamoto et al. | 424/400 |

FOREIGN PATENT DOCUMENTS 0491953 7/1992 European Pat. Off. .

OTHER PUBLICATIONS

Patent Abstracts of Japan, vol. 7, No. 281-JP58158145.
Database WPIL-Section Ch, Week 9047-90-352830.
Database WPIL-Section Ch, Week 9046-90-345705.
Database WPIL-Section Ch, Week 8748-87-337070.

*Primary Examiner*—Jeanette Hunter
*Attorney, Agent, or Firm*—Sughrue, Mion, Zinn, Macpeak & Seas

[57] ABSTRACT

Disclosure is a method for converting maltitol into crystalline powder by very simple procedures and in short time. To an aqueous solution of maltitol with 1-15% by weight of moisture content, seed crystals of maltitol are added and a shearing force is applied continuously at a temperature lower than the melting point of the seed crystals, thus obtaining a powdery crystalline maltitol.

6 Claims, No Drawings

METHOD FOR MANUFACTURING POWDERY CRYSTALLINE MALTITOL

BACKGROUND OF THE INVENTION

1. Field of the Invention

The present invention relates to a method for manufacturing powdery crystalline maltitol.

2. Description of the Prior Art

Maltitol has been utilized as a sweetening agent in low-calorie foods, diet foods, low cariogenic foods and foods for diabetic patients since it will not be easily digested and absorbed in the human digestive canal and also not easily fermented by oral bacteria.

However, maltitol has been inconvenient in handling since its dried products are extremely hygroscopic, deliquescent and difficult to powder.

With a view to overcoming this problem, a number of techniques have been proposed for implementing the crystallization or powderization of maltitol.

More specifically, for example, a method was disclosed in Japanese Patent Publication No. 2439/1988, in which seed crystals are added into a highly concentrated maltitol solution for crystallizing out anhydrous crystalline maltitol. This method characterized in that a high purity crystalline maltitol can be obtained, but it gives only low yield, showing low workability.

Japanese Patent Publication No. 11599/1990 and Japanese Patent Laid-Open Publication No. 180795/1986 proposed methods in which maltitol obtained by hydrogenation of maltose is submitted to chromatography for increasing purity and then crystalline maltitol is separated from the concentrated solution of this purified maltitol. The methods, however, are also problematic in regard to yield and workability.

A method was disclosed in Japanese Patent Laid-Open Publication No. 268696/1986, wherein a mass consisting of maltitol syrup and crystals is made to flow through a gradient crystallizing-out zone the temperature of which has been lowered and the separated crystals are collected. A large-sized apparatus is required and payability is low.

According to Japanese Patent Publication No. 7349/1991, seed crystals are added to a highly concentrated maltitol solution at a high temperature, and after adjusting the moisture content to 2–15% by weight, the mixture is gradually cooled so as to solidify the maltitol, and the solid is roughly broken, as required, followed by drying, and thereafter powderized into desired particle sizes, thus making maltitol products as a commodity. In this method, an aqueous solution of 70% maltitol is concentrated to 4% of moisture content and, after powdery maltitol is added thereto, the mixture is cooled from 90° C. to room temperature over about 20 hours for solidification. No description is given on application of shearing force for the solidification. In this method a long time is required for the solidifying and crystallizing processes and a large amount of energy is required for cutting and pulverizing the solid matter there obtained.

Japanese Patent Publication No. 47140/1989 disclosed a method, wherein a concentrated solution of hydrogenated maltose is placed in a tray and crystals are added and the mixture, after thoroughly kneaded, is kept hot for allowing crystallization to proceed and plasticity to appear, and thereafter the product is extruded through nozzles, followed by cooling, and cut into granular maltitol. This method also requires a long time for crystallization and a great amount of energy for cutting solidified maltitol.

SUMMARY OF THE INVENTION

The purpose of the present invention is to provide a method of manufacturing powdery or granular crystalline maltitol by simple procedures and with high efficiency.

In order to achieve the aforementioned purpose, according to the present invention, there is provided a method for manufacturing powdery or granular crystalline maltitol, comprising the steps of: adding seed crystals of maltitol at a temperature lower than the melting point of the seed crystals of maltitol to an aqueous solution of maltitol with 1–15% by weight of moisture content; kneading the mixture in the presence or absence of additives selected from the group consisting of a fat, an oil and a surface-active agent; and continuously applying a shearing force to the kneaded mass.

DETAILED DESCRIPTION OF THE INVENTION

The present invention relates to a method of manufacturing a powdery crystalline maltitol in which comprises adding seed crystals of maltitol at a temperature lower than the melting point of the seed crystals of maltitol to an aqueous solution of maltitol with 1–15% by weight of moisture content; kneading the mixture in the presence or absence of additives selected from the group consisting of a fat, an oil and a surface-active agent; and continuously applying a shearing force to the kneaded mass.

The aqueous solution of maltitol used in the present invention is a viscous liquid or a starch-syrup-like viscous liquid with 1–15% by weight of moisture content. The maltitol obtainable by ordinary methods is not in powder even in a state of such extremely low moisture content. Such a highly concentrated aqueous solution of maltitol may be a non-cooled product (ordinarily having a temperature higher than 100° C.) that can be obtained by thickening and dehydrating an aqueous solution of maltitol in low concentration to or one by thermally melting an amorphous solid of maltitol and then adjusting its moisture content.

The aqueous solution of maltitol used in the present invention is preferably at higher purities of maltitol, normally at not less than 80% by weight of maltitol in the solid matter, and more preferably at not less than 85% by weight.

The moisture content of the aqueous solution of maltitol is 1–15% by weight, more preferably 3–10% by weight. It is essential that raw maltitol to be crystallized contain moisture, which is an essential condition of the present invention. When moisture content is close to 0, the solution remains to be a viscous liquid even upon continuous application of shearing force such that powdery maltitol cannot be obtained. When the moisture content exceeds 15% by weight, the powderization may be possible depending on conditions, but even in such a case a considerably long time is required for powderization.

The moisture content for the present invention is preferably 3–10% by weight in view of workability (crushability of solid matter and load on the kneader) and time required for powderization.

Smoother powderization of maltitol may be performed in the present invention by adding additives such as a fat, an oil and a surface-active agent to the aqueous solution of maltitol. The amount of the fat, oil and surface-active agent to be added is no more than 30%, preferably 0.5–20%, and more preferably 1.0–10%. Setting such a condition that the sum of moisture content and the content of the additives becomes not less than 3% will facilitate the powderization.

The addition of the additives such as the fat, oil, and surface-active agent causes maltitol and the additives to be formed into an emulsion, making it possible to keep the fluidity of molten maltitol even at relatively low temperatures. As a result, even with temperature of solution lowered by the addition of seed crystals, agitation of the system is still easy causing no local solidification and allowing uniform dispersion of the seed crystals to be readily accomplished. Also use of a large amount of seed crystals becomes possible.

Examples of the additives that may be used in the present invention are vegetable oils, animal oils, hydrogenated oils, mineral oils, waxes (esters of higher fatty acids and higher alcohols) and the like, and vegetable oils, particularly triglycerides are preferable such as rape seed oil, soybean oil, cotton seed oil, palm oil, corn oil, rice bran oil, safflower oil, peanut oil, olive oil, castor oil and jojoba oil.

For the surface-active agent, not limitative, since powdery maltitol is most frequently used in the fields of pharmaceuticals and foods, those that have been used as food additives, materials of pharmaceuticals or cosmetics may be exemplified, for example, fatty acid esters of glycerol such as monoglycerides, diglycerides and the like, fatty acid esters of sucrose, fatty acid esters of sorbitan, fatty acid esters of propyleneglycol, fatty acid esters of polyglycerol, fatty acid esters of polyoxyethylenesorbitan, oxyethylenefatty alcohols, fatty acid esters of pentaerythritol, lecithin, higher fatty acid soaps, and saponins.

For applications other than foods and pharmaceuticals, almost all of surface active agents may be used, and examples are polyoxyalkylene aliphatic alcohols, polyoxyalkylene alkylphenyl ethers, polyoxyalkylene aliphatic amides, and polyoxyethylene/polyoxypropylene random or block copolymers, and sulfuric acid esters of the above ether-type nonionic surface active agents, polyalkyleneglycol fatty acid esters and fatty acid alkanolamides.

The above additives may be added previously in a highly concentrated maltitol solution or added to maltitol prior to the addition of seed crystals. They may also be used in a way that seed crystals are dispersed in the additives.

The amount of the additives to be used, varying depending on the sort of the additives, is preferably not less than 0.5% by weight relative to the amount of maltitol solid content in the aqueous solution of maltitol, and particularly use of more than 1% by weight reveals a prominent effect. Use of more than 30% by weight does not give better effect. With regard to the purity of crystalline maltitol as small amount of the additives to be used as possible is better so far as the desired effect is secured, but when the powdery maltitol is used as an additive for producing surimi (raw fish-meat paste) a larger amount of the additives may be used since the case is such that the additives themselves are useful.

Into the aqueous solution of maltitol to which the additives have been added, seed crystals of maltitol are added during agitation. The temperature of the maltitol solution during the addition is lower than the melting point of the seed crystals of maltitol, for example lower than 140° C., preferably lower than 130° C., and it may be lowered to an extent where viscosity of the solution has been raised so that agitation and kneading become impossible, but ordinarily it is higher than 20° C., preferably higher than 50° C., and particularly preferably in the range of 50°–120° C. The seed crystals of maltitol, which contain a high content of anhydrous crystalline maltitol, are ordinarily required to have a purity of higher than 80% by weight, but they may contain, as minor contaminants, crystalline sorbitol, crystalline maltotriitol, crystalline maltotetraitol, and the like. The amount of seed crystals to be added has only to be such an amount that the present invention can be achieved with regard to the time required for powderization of maltitol, and ordinarily it is 1–50% by weight of the total amount of powdery crystalline maltitol.

The moisture content of seed crystals of maltitol is not more than 10% by weight, and preferably not more than 5% by weight.

The most characteristic feature of the present invention is that merely by continuously applying a shearing force to a kneaded mass after the addition of seed crystals of maltitol to aqueous solution of maltitol, powdery crystalline maltitol can be obtained continuously and yet at high yield, which has been attained only under the conditions specified in the present invention. It is noted that, for applying a shearing force in the present invention, a mixer that has a crushing mechanism in addition to agitating and kneading mechanisms is employed. Examples are a cokneader, double arm kneader, ribbon-type mixer, screw-type mixer, paddle mixer, Muller mixer, radial rod mixer, pin mixer, botater, self-screening mixer, cracker, rapid kneader, universal mixer, cutter mixer, Shuggy mixer, pug mill, mix muller, multimull, wet-pan mill, Irich mill, crutcher and internal mixer. Among them, the so-called kneaders, exemplified by the cokneader and the double arm kneader, are preferably used by virtue of their better workability. Both batch type and continuous type mixers may be used and in view of productivity the continuous type is preferable.

The kneaded mass of aqueous solution of maltitol and seed crystals of maltitol is solidified by continuously applying a shearing force thereto in such a mixer, over the steps of being converted into a paste and then a plastic mass, and finally is powderized. The time required for these changes, varying depending on conditions, is ordinarily about 1–120 minutes. Needless to say, it is possible to add seed crystals in the same mixer. The crystalline maltitol may be directly graded to make a product, but it is also possible to submit to an extruding granulator for making granules of desired sizes. The moisture content of the powdery or granular crystalline maltitol obtained is ordinarily less than 10% by weight, preferably less than 5% by weight, and excessive moisture may be removed by drying.

The present invention is now illustrated in more detail with reference to its examples.

EXAMPLE 1

An amount of 490 g of each aqueous solution of maltitol (purity of maltitol in the solid matter: 92%), which had been dehydrated to their respectively specified moisture contents, were each placed in a 2-liter double arm kneader (jacket temperature: 90° C.), and after adding 210 g of seed crystals of maltitol at a temperature of about 105° C., the mass was continuously kneaded and their state was observed with time. The results are shown in Table 1.

TABLE 1

| Formula | a | b | c | d | e | f | g | h | i | j |
|---|---|---|---|---|---|---|---|---|---|---|
| Moisture content in aqueous maltitol solution (%) | 1.5 | 2.0 | 2.2 | 2.4 | 4.7 | 7.4 | 9.4 | 11.4 | 14.7 | 16.7 |
| Moisture content of whole formula (%) | 1.1 | 1.4 | 1.5 | 1.7 | 3.3 | 5.2 | 6.6 | 8.0 | 10.3 | 11.7 |
| Moisture content of product (%) | — | 0.7 | 0.8 | 1.0 | 1.6 | 2.1 | 2.4 | 2.7 | 3.4 | — |
| Working efficiency | | | | | | | | | | |
| Crushability of solid matter | — | x~Δ | x~Δ | Δ | ○ | ⊚ | ⊚ | ⊚ | ⊚ | — |
| Load on kneader | Slightly large | Large | Slightly large | Slightly large | Small | Small | Small | Small | Small | Small |
| Time required for powderization (min.) | N.P. | 6.0 | 5.5 | 7.4 | 5.2 | 9.5 | 13.8 | 26.3 | 32.6 | >120 |

Crushability of solid matter: ⊚: Very good; ○: Good; Δ: Slightly poor; x: Poor.
N.P.: Not powderized.

EXAMPLE 2

To an aqueous solution of maltitol (purity of maltitol in the solid matter: 92%), which had been dehydrated to a moisture content of 4.7%, seed crystals of maltitol were added in different rates and change of the mixtures with time was observed in the same manner as in Example 1. The results are shown in Table 2.

TABLE 2

| Formula | k | l | m | e' | n |
|---|---|---|---|---|---|
| Aqueous maltitol solution (%) | 99 | 95 | 85 | 70 | 50 |
| Seed crystals of maltitol (%) | 1 | 5 | 15 | 30 | 50 |
| Moisture content of aqueous maltitol solution (%) | 4.7 | 4.7 | 4.7 | 4.7 | 4.7 |
| Moisture content of whole formula (%) | 4.7 | 4.5 | 4.0 | 3.3 | 2.4 |
| Moisture content of product (%) | 2.2 | 2.1 | 1.7 | 1.6 | 1.6 |
| Workability | | | | | |
| Crushability of solid matter | x~Δ | Δ | Δ~○ | ○ | Δ~○ |
| Load on kneader | Slightly large | Slightly large | Small | Small | Small |
| Time required for powderization (min.) | 15.2 | 13.8 | 7.5 | 5.3 | 1.3 |

EXAMPLE 3

To an aqueous solution of maltitol (purity of maltitol in the solid matter: 92%), which had been dehydrated to a moisture content of 4.0% or 2.0%, palm oil-monoglyceride (monoglyceride derived from palm oil, a mixture of monoglyceride:diglyceride:triglyceride=45:40:15) were added at specified amounts for the formation of dispersions, and with 10% or 30% of seed crystals of maltitol added, and their state was observed with time in the manner similar to the Example 1. The results are shown in Tables 3 and 4.

TABLE 3

| Formula | o | p | q | r | s |
|---|---|---|---|---|---|
| Aqueous maltitol solution (%) | 90 | 89.4 | 88.5 | 85.8 | 68.6 |
| Palm oil monoglyceride (%) | 0 | 1.0 | 2.0 | 5.0 | 2.0 |
| Seed crystals of maltitol (%) | 10 | 9.6 | 9.5 | 9.2 | 29.4 |
| Moisture content of aqueous maltitol solution (%) | 4.0 | 4.0 | 4.0 | 4.0 | 4.0 |
| Moisture content of whole formula (%) | 3.6 | 3.6 | 3.5 | 3.4 | 2.7 |
| Moisture content of product (%) | 1.5 | 1.6 | 1.5 | 1.6 | 1.8 |
| Workability | | | | | |
| Crushability of solid matter | Δ | Δ | Δ~○ | ○ | ○ |
| Load on kneader | Slightly large | Small | Small | Small | Small |
| Time required for powderization (min.) | 6.3 | 6.7 | 6.8 | 6.7 | 3.5 |

TABLE 4

| Formula | t | u | v | w |
|---|---|---|---|---|
| Aqueous maltitol solution (%) | 69.3 | 68.6 | 67.9 | 66.5 |
| Palm oil monoglyceride (%) | 1.0 | 2.0 | 3.0 | 5.0 |
| Seed crystals of maltitol (%) | 29.7 | 29.4 | 29.1 | 28.5 |
| Moisture content of aqueous maltitol solution (%) | 2.0 | 2.0 | 2.0 | 2.0 |
| Moisture content of whole formula (%) | 1.4 | 1.4 | 1.4 | 1.3 |
| Moisture content of product (%) | 0.7 | 0.7 | 0.8 | 0.8 |
| Workability | | | | |
| Crushability of solid matter | x~Δ | Δ | Δ~○ | ○ |
| Load on kneader | Slightly large | Small | Small | Small |
| Time required for powderization (min.) | 5.7 | 3.9 | 4.0 | 4.0 |

EXAMPLE 4

The same experiments as in Example 3 were conducted except that the palm oil monoglyceride was replaced by fatty acid ester of propyleneglycol (Rikemal PO-100, made by Riken Vitamins) or hydrogenated rape seed oil (Bellcoat N, made by Kanegafuchi Kagaku Kogyo K. K.). Results showed that when fatty acid ester of propyleneglycol and hydrogenated rape seed oil were used, the time required for powderization was 8 and 5 minutes, respectively, and workability was also superior.

EXAMPLE 5

An amount of 2400 g each of aqueous solutions of maltitol (purity of maltitol in the solid matter: 92%), which had been dehydrated to a moisture content of 7.4%, were placed in a 6-liter double arm kneader whose jacket was warmed at specified temperature, and 600 g of seed crystals of maltitol were added at a temperature of 105° C. and the mixtures were continuously kneaded while their change was observed with time. Results are shown in Table 5.

TABLE 5

| Jacket temperature (°C.) | 85 | 65 | 45 | 20 |
|---|---|---|---|---|
| Moisture content in aqueous maltitol solution (%) | 7.4 | 7.4 | 7.4 | 7.4 |
| Moisture content of whole formula (%) | 5.9 | 5.9 | 5.9 | 5.9 |
| Moisture content of product (%) | 1.4 | 2.2 | 2.2 | 2.8 |
| Workability | | | | |
| Crushability of solid matter | ⊙ | ○ | Δ~○ | x~Δ |
| Load on kneader | Small | Small | Small | Slightly large |
| Time required for powderization (min.) | 11.3 | 8.7 | 8.2 | 6.5 |

EXAMPLE 6

With the same formula as in Example 1 used for experiments except that an aqueous solution of maltitol (purity of maltitol in the solid matter: 88%) was used, the change with time was observed. The time required for powderization was about 30 minutes and workability was good.

EXAMPLE 7

When 36.8 kg of an aqueous solution of maltitol (purity of maltitol in the solid matter: 90%, moisture content: 8.2%) and 16.9 kg of seed crystals of maltitol were fed together into a double-axle continuous kneader (jacket temperature: 90° C.) at a feeding rate of 5.5 kg/min, powderization was completed in a staying time of 20 minutes. The moisture content of the product was 3.3%, while it showed successful fluidity and stability.

EXAMPLE 8

When the powdery crystalline maltitol obtained in Example 7 was dried in a shelf-type fan drier at 70° C. for 4 hours, the moisture of the product was 0.53%. When the maltitol from Example 7 was granulated without drying by an extruding granulator, granules with good dispersibility and solubility in water were obtained.

According to the method of the present invention, maltitol, which heretofore has been so hygroscopic that it is difficult to handle, can be converted into crystalline powder by simple procedures and in short time, and the powdery maltitol thus obtained is low in hygroscopicity and easy to handle.

What is claimed is:

1. A method for manufacturing powdery or granular crystalline maltitol, which comprises adding seed crystals of maltitol at a temperature lower than the melting point of the seed crystals of maltitol to an aqueous solution of maltitol with 1-15% by weight of moisture content; kneading the mixture in the presence or absence of additives selected from the group consisting of a fat, an oil and a surface-active agent; and continuously applying a shearing force to the kneaded mass.

2. A method as claimed in claim 1, wherein the purity of maltitol in the powdery or granular crystalline maltitol is not less than 80% by weight on solid matter basis.

3. A method as claimed in claim 1, wherein the moisture content of the aqueous solution of maltitol is 3-10% by weight.

4. A method as claimed in claim 1, wherein the temperature at the time of applying a shearing force is 50°-120° C.

5. A method as claimed in claim 1, wherein the amount of the seed crystals to be added is 1-50% by weight of the content of powdery crystalline maltitol that is finally obtained.

6. A method as claimed in claim 1, wherein the amount of the additives is not more than 30% by weight of the total amount of solid matter in the aqueous solution of maltitol.

* * * * *